(12) United States Patent
King et al.

(10) Patent No.: US 9,657,130 B1
(45) Date of Patent: May 23, 2017

(54) POLYURETHANE MATERIALS FORMED FROM UNSATURATED PLANT OILS VIA AN ALKYNE ZIPPER REACTION

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/965,263

(22) Filed: Dec. 10, 2015

(51) Int. Cl.
| | | |
|---|---|---|
| *C08G 18/32* | (2006.01) | |
| *C08G 18/72* | (2006.01) | |
| *C08G 101/00* | (2006.01) | |
| *C07C 29/147* | (2006.01) | |
| *G10K 11/162* | (2006.01) | |

(52) U.S. Cl.
CPC ........ *C08G 18/3206* (2013.01); *C07C 29/147* (2013.01); *C08G 18/72* (2013.01); *G10K 11/162* (2013.01); *C08G 2101/00* (2013.01); *C08G 2350/00* (2013.01)

(58) Field of Classification Search
CPC C08G 18/3206; C08G 18/72; C08G 2101/00; C08G 2350/00; C07C 29/147; G10K 11/162
See application file for complete search history.

(56) References Cited

U.S. PATENT DOCUMENTS

| | | | |
|---|---|---|---|
| 2,902,398 | A | 9/1959 | Schroeder |
| 3,058,921 | A | 10/1962 | Pannell |
| 3,829,522 | A | 8/1974 | Schneider |
| 4,474,944 | A | 10/1984 | Yasuda et al. |
| 8,592,498 | B2 | 11/2013 | Enomura |
| 2011/0060076 | A1 | 3/2011 | Hefner, Jr. et al. |

FOREIGN PATENT DOCUMENTS

| | | |
|---|---|---|
| CN | 103435870 A | 12/2013 |
| CN | 104059032 A | 9/2014 |
| CN | 104130145 A | 11/2014 |
| CN | 104530335 A | 4/2015 |
| CN | 103265708 B | 7/2015 |
| CN | 104804164 A | 7/2015 |
| JP | S58179226 A | 10/1983 |

OTHER PUBLICATIONS

Hojabri, et al., "Fatty Acid-Derived Diisocyanate and Biobased Polyurethane Produced from Vegetable Oil: Synthesis, Polymerization, and Characterization", American Chemical Society, Biomacromolecules 2009, vol. 10,, pp. 884-891.

Zlatanic, et al., "Structure and Properties of Triolein-Based Polyurethane Networks", American Chemical Society, Biomacromolecules, 2002, vol. 3, pp. 1048-1056.

*Primary Examiner* — Rabon Sergent

(74) *Attorney, Agent, or Firm* — Patterson + Sheridan, LLP

(57) ABSTRACT

A process of forming a polyurethane material includes forming an unsaturated alcohol from an unsaturated plant oil via a reduction reaction. The process includes forming an alkyne-terminated alcohol from the unsaturated alcohol and forming a polyol having two primary hydroxyl groups from the alkyne-terminated alcohol. The process further includes polymerizing a mixture that includes the polyol having the two primary hydroxyl groups to form a polyurethane material.

19 Claims, 2 Drawing Sheets

POLYURETHANE MATERIALS FORMED FROM UNSATURATED PLANT OILS VIA AN ALKYNE ZIPPER REACTION

I. FIELD OF THE DISCLOSURE

The present disclosure relates generally to biorenewable polyurethane materials.

II. BACKGROUND

Vegetable oils may be used to form polyols. Such vegetable oil-based polyols may be used as derivatives for polyurethanes. However, these polyols typically produce polyurethanes with poor mechanical properties compared to petroleum-based polyurethanes.

III. SUMMARY OF THE DISCLOSURE

According to an embodiment, a process of forming a polyurethane material includes forming an unsaturated alcohol from an unsaturated plant oil via a reduction reaction. The process includes forming an alkyne-terminated alcohol from the unsaturated alcohol and forming a polyol having two primary hydroxyl groups from the alkyne-terminated alcohol. The process further includes polymerizing a mixture that includes the polyol having the two primary hydroxyl groups to form a polyurethane material.

According to another embodiment, a biorenewable polyurethane material is disclosed. The biorenewable polyurethane material is formed by a process that includes forming unsaturated alcohols from an unsaturated plant oil via a reduction reaction. The process also includes forming alkyne-terminated alcohols from the unsaturated alcohols and forming polyols having two primary hydroxyl groups from the alkyne-terminated alcohols. The process further includes polymerizing a mixture that includes the polyols having the two primary hydroxyl groups to form a biorenewable polyurethane material.

According to another embodiment, an acoustic dampening foam is disclosed. The acoustic dampening foam includes a petroleum-based polyurethane material and a biorenewable polyurethane material. The biorenewable polyurethane material is formed by a process that includes forming unsaturated alcohols from an unsaturated plant oil via a reduction reaction, forming alkyne-terminated alcohols from the unsaturated alcohols, and forming polyols having two primary hydroxyl groups from the alkyne-terminated alcohols. The process also includes polymerizing a mixture that includes the polyols having the two primary hydroxyl groups to form a biorenewable polyurethane material. The process further includes chemically reacting the polyurethane material with a diisocyanate cross-linking material to form the biorenewable polyurethane material.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

IV. BRIEF DESCRIPTION OF THE DRAWINGS

Figure 1:
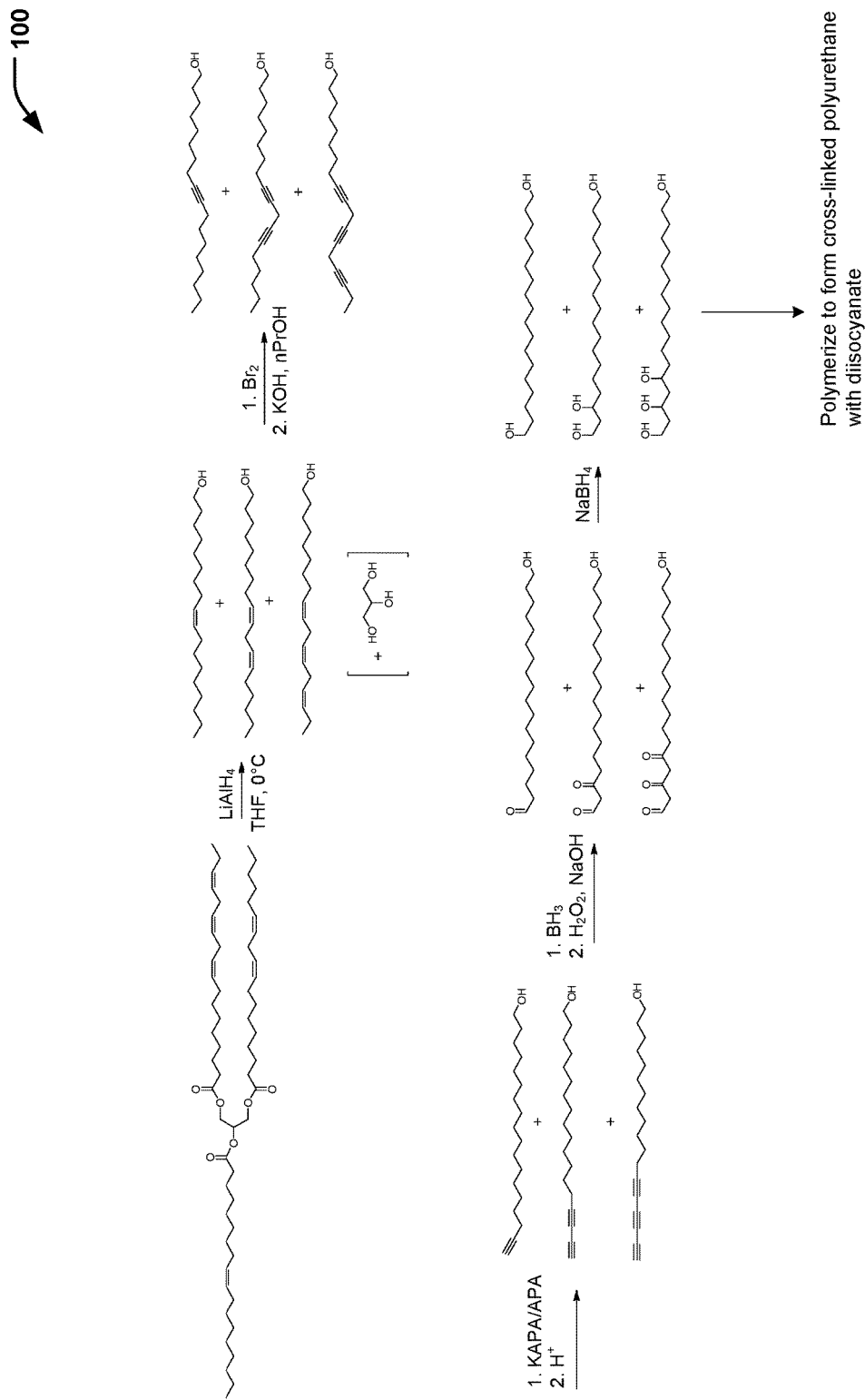
Figure 2:
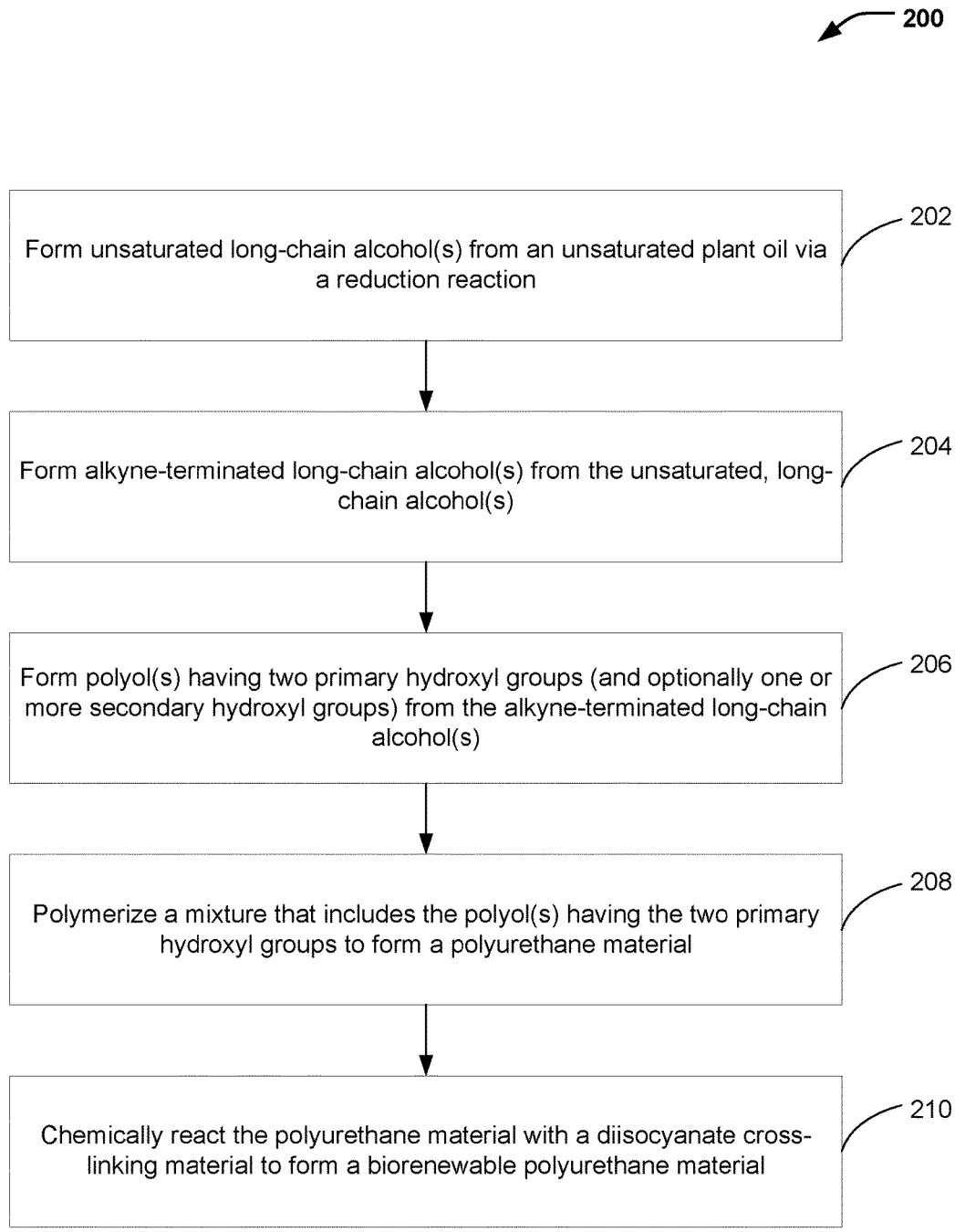

FIG. 1 is a chemical reaction diagram showing the preparation of a biorenewable polyurethane material, according to one embodiment; and FIG. 2 is a flow diagram showing a particular embodiment of a process of forming a biorenewable polyurethane material.

V. DETAILED DESCRIPTION

The present disclosure relates to polyurethane materials and methods of forming polyurethane materials from biorenewable materials (e.g., plant oils, such as vegetable oils). Vegetable oils include a mixture of triglycerides (made up of three fatty acids), and these compositions may vary according to the source of the oil. There are relatively inexpensive and readily available unsaturated vegetable oils (UVOs) that include relatively small amounts of saturated fatty acids. In the present disclosure, each unsaturated fatty acid component of highly unsaturated UVOs is converted into long-chain alcohols with terminal, primary hydroxyl groups and no terminal aliphatic chains (also referred to as "dangling chains"). In the present disclosure, the UVOs are converted to long-chain alcohols, and alkenes in the long-chain alcohols are converted to alkynes via a subsequent bromination and "double" elimination reaction. The alkynes, which are internal at this point, are converted to terminal alkynes through the use of an alkyne zipper reaction. A mixture of polyols is then synthesized by converting the alkynes to hydroxyl groups via a number of different methods including hydroboration and reduction/epoxidation/ring-opening. Polyurethanes are formed from these polyols by reaction with a diisocyanate. The process of reducing these terminal alkyl chains simultaneously increases the overall amount of primary hydroxyl group content.

Some biorenewable polyurethane materials may have deleterious mechanical properties. As a result, such biorenewable polyurethane materials may be diluted with other non-renewable polyurethane materials in order to achieve desired material properties. The poor mechanical properties of biorenewable polyurethanes may result from a low ratio of primary to secondary hydroxyl groups and an abundance of terminal aliphatic alkyl chains (also referred to as "dangling chains"). In the present disclosure, plant oils (e.g., vegetable oils) may be converted into long-chain alcohols, and an "alkyne zipper reaction" may be used to convert internal alkenes of the long-chain alcohols into terminal alkynes. The terminal alkynes may be converted into terminal, primary hydroxyl groups (with no dangling chains). The elimination of the presence of the terminal aliphatic alkyl chains in the polyols of the present disclosure may enable formation of biorenewable polyurethane materials with improved mechanical properties.

Referring to FIG. 1, a chemical reaction diagram 100 illustrates the preparation of a polyurethane material from an unsaturated plant oil (e.g., an unsaturated vegetable oil, or UVO), according to one embodiment. In the example of FIG. 1, the unsaturated plant oil includes unsaturated linseed oil. In other embodiments, alternative and/or additional unsaturated plant oils (e.g., soybean oil, castor oil, etc.) may be used. The first chemical reaction (proceeding from left to right) shown in FIG. 1 illustrates that an unsaturated plant oil may be reduced to three unsaturated, long-chain alcohols (and glycerol, which may be optionally carried through in one or more subsequent chemical reactions). The second chemical reaction shown in FIG. 1 illustrates that the internal alkene groups (i.e., carbon-carbon double bonds) in the unsaturated, long-chain alcohols may be converted to internal alkyne groups (i.e., carbon-carbon triple bonds). The third chemical reaction shown in FIG. 1 illustrates that the internal alkyne groups may be converted to terminal alkynes. The fourth chemical reaction shown in FIG. 1 illustrates that the terminal alkynes may be converted into carbonyl groups. The fifth chemical reaction shown in FIG. 1 illustrates that the carbonyl groups may be reduced to hydroxyl groups. The resulting polyol mixture includes polyols that include no "dangling chains" and multiple hydroxyl groups per long-chain alcohol. FIG. 1 further illustrates that the mixture of polyols may be polymerized to form a cross-linked polyurethane material via a chemical reaction with a diisocyanate material.

Vegetable oils or triglycerides, especially those that include alkenes on each of their three fatty-acid chains may be used, as a fatty acid that includes an alkene results in a terminal, primary hydroxyl group (with no dangling chains). There may be zero or multiple secondary hydroxyl groups present, depending on the particular plant oil and the number of double bonds that the particular plant oil contains. Secondary hydroxyl groups increase the OH-number of the resulting polyol, thereby increasing the extent of cross-linking that is achievable in the final polyurethane material.

Examples of oils that may be utilized include oils that have a high average number of double-bonds per triglyceride. Illustrative, non-limiting examples of such oils include canola oil (3.9 double-bonds per triglyceride), corn oil (4.5 double-bonds per triglyceride), cottonseed oil (3.9 double-bonds per triglyceride), linseed oil (6.6 double-bonds per triglyceride), olive oil (2.8 double-bonds per triglyceride), soybean oil (4.6 double-bonds per triglyceride), and tung oil (7.5 double-bonds per triglyceride). Other examples include rapeseed oil (with a high oleic/linoleic/linoleic acid content, corresponding to a higher double bond content), refined tall oil, and sunflower oil.

The UVO illustrated at the top left of FIG. 1 includes at least one alkene group (i.e., a carbon-carbon double bond) on each of its fatty acid chains. For example, a first fatty acid chain (left side) of the UVO includes one alkene group, a second fatty acid chain (bottom right side) of the UVO includes two alkene groups, and a third fatty acid chain (top right side) of the UVO includes three alkene groups. It will be appreciated that alternative numbers and/or arrangements of alkene groups may be present in an unsaturated vegetable oil. The first chemical reaction of FIG. 1 illustrates that the UVO may be reduced with a suitable reducing agent (e.g., lithium aluminum hydride). Such reduction converts the triglyceride esters to hydroxyl groups, resulting in three unsaturated, long-chain alcohols (and a glycerol byproduct). For example, a first unsaturated, long-chain alcohol (corresponding to the first fatty acid chain) includes one internal alkene group and a terminal, primary hydroxyl group. A second unsaturated, long-chain alcohol (corresponding to the second fatty acid chain) includes two internal alkene groups and a terminal, primary hydroxyl group. A third unsaturated, long-chain alcohol (corresponding to the third fatty acid chain) includes three internal alkene groups and a terminal, primary hydroxyl group.

The second chemical reaction of FIG. 1 illustrates that the three unsaturated, long-chain alcohols are subjected to dehydrohalogenation conditions, converting each alkene into an alkyne (i.e., a carbon-carbon triple bond) via subsequent bromination and elimination reactions. For example, FIG. 1 illustrates that the single alkene group of the first unsaturated, long-chain alcohol is converted to one alkyne group, the two alkene groups of the second unsaturated, long-chain alcohol are converted to two alkyne groups, and the three alkene groups of the third unsaturated, long-chain alcohol are converted into three alkyne groups. In a particular embodiment, the glycerol byproduct formed in the first chemical reaction may be retained in the second chemical reaction and subsequently removed prior to the third chemical reaction.

The third chemical reaction of FIG. 1 illustrates that the internal alkynes of the long-chain alcohols are then converted into terminal alkynes via the "acetylene zipper" reaction, followed by an aqueous or acidic work-up. To illustrate, in the example of FIG. 1, the "zipper" reaction shifts the position of the internal alkyne group of the first long-chain alcohol to an end of the chain (opposite the terminal, primary hydroxyl group), shifts the positions of the two internal alkyne groups of the second long-chain alcohol to the end of the chain (opposite the terminal, primary hydroxyl group), and shifts the three internal alkyne groups of the third long-chain alcohol to the end of the chain (opposite the terminal, primary hydroxyl group). FIG. 1 depicts an illustrative example in which the "outermost" alkyne group (furthest from the terminal, primary hydroxyl group) of each long-chain alcohol is shifted to the end of the carbon chain (forming the "terminal" alkyne). In the case of the second and third long-chain alcohols having one or more additional alkyne groups, the "inner" alkyne(s) are shifted to position(s) adjacent to the terminal alkyne. In other cases, the "inner" alkyne(s) may be shifted to alternative position(s) along the carbon chain that are not directly adjacent to the "terminal" alkyne.

The fourth chemical reaction of FIG. 1 illustrates that the alkynes are then converted into carbonyl groups under hydroboration reaction conditions, where each terminal alkyne is converted into an aldehyde and each internal alkyne is converted into a ketone. To illustrate, the first long-chain alcohol includes no internal alkynes and a terminal alkyne that is converted into an aldehyde, the second long-chain alcohol includes one internal alkyne (adjacent to the terminal alkyne that is converted into an aldehyde) that is converted into a ketone, and the third long-chain alcohol includes two internal alkynes (adjacent to the terminal alkyne that is converted into an aldehyde) that are converted into ketones.

The fifth chemical reaction of FIG. 1 illustrates that the carbonyl groups are then reduced to hydroxyl groups using a suitable reducing agent (e.g., sodium borohydride in the example of FIG. 1) to form a mixture of polyols that include no "dangling chains" and two primary hydroxyl groups per reduced fatty acid chain. To illustrate, the first polyol (corresponding to the first reduced fatty acid chain of the UVO) includes two primary hydroxyl groups and no secondary hydroxyl groups, the second polyol (corresponding to the second reduced fatty acid chain of the UVO) includes two primary hydroxyl groups and one secondary hydroxyl group, and the third polyol (corresponding to the third reduced fatty acid chain of the UVO) includes two primary hydroxyl groups and two secondary hydroxyl groups.

FIG. 1 further illustrates that the polyol mixture may be polymerized to form a cross-linked polyurethane material. For example, the polyol mixture may be mixed with a diisocyanate material (and potentially water or another foaming additive) and polymerized in accordance with various polyurethane fabrication procedures. Illustrative examples of diisocyanate materials for use as cross-linking materials may include methylene diphenyl diisocyanate (MDI), toluene diisocyanate (TDI), hexamethylene diisocyanate (HDI), isophorene diisocyanate (IPDI), pentamethylene diisocyanate (PDI), or a combination thereof (among other alternatives). A degree of cross-linking in the cross-linked polyurethane material may be controlled by adjusting an amount of diisocyanate material (e.g., stoichiometric or sub-stoichiometric amounts) that is reacted with a polyurethane material formed from the polyol mixture. To illustrate, a degree of polymerization of the polyurethane material may be adjusted such that a subset of hydroxyl groups of a plurality of hydroxyl groups of the polyol molecules remain available for chemical reaction with the diisocyanate material.

In a particular embodiment, the cross-linked biologically-based polyurethane material formed according to the process illustrated in FIG. 1 may be used as a component of an acoustic dampening foam (e.g., for mainframe servers). For example, an acoustic dampening foam may include a petroleum-based polyurethane material and a biologically-based polyurethane material. A weight percentage of the biologically-based polyurethane material may be not less than 10 weight percent of the acoustic dampening foam. Thus, in some cases, the biologically-based polyurethane materials of the present disclosure may allow for a reduction in an amount of petroleum-based polyurethane materials while satisfying particular mechanical property standards. The weight percentage may be adjusted based on desired mechanical properties for the acoustic dampening foam. Illustrative, non-limiting examples of desired material properties may include a density of about 2 pounds per cubic foot, a pore count of about 65-75 pores per inch, and a biorenewable content of at least 10 weight percent. In the context of fabric-over-foam gaskets, a desired material property may be a compression set of less than 5 percent following compression to 50 percent of an initial thickness.

Prophetic Example

Reduction of Triglyceride Esters

To a stirred suspension of $LiAlH_4$ (4 equivalents) in 500 mL of anhydrous tetrahydrofuran (THF) at about 0° C., a solution of natural oil (1 equivalent) in 50 mL of anhydrous THF may be added, dropwise. The reaction mixture may be stirred (e.g., for about 4 hours) and quenched by slow, dropwise addition of 2N HCl. The solids may be removed by filtration, and the layers of the filtrate may be separated. The aqueous layer may be rinsed with $NaHCO_3$, brine, and dried over $MgSO_4$. The solvent may be removed in vacuo, and the resulting crude product may be purified by vacuum distillation or other techniques, resulting in a mixture of unsaturated long chain alcohols.

Prophetic Example

Conversion of Alkenes to Alkynes

The crude mixture of unsaturated long-chain alcohols (and optionally the glycerol byproduct) may be dissolved in diethyl ether (0.2 M) and cooled to about −10° C. with an ice/NaCl bath. While stirring, bromine (in slight excess relative to the number of unsaturations) may be added dropwise, maintaining a reaction temperature below about −5° C. Upon completion of the addition, the cooling bath may be removed, and the reaction may be stirred for about 2 hours. The additional bromine may be quenched by the addition of a saturated sodium thiosulfate solution, and the layers may be separated. The aqueous layer may be rinsed with diethyl ether (e.g., 3 times), and the combined organic layers may be rinsed with water (e.g., 2 times), brine, and dried over $MgSO_4$. The solvent may be removed in vacuo, and the resulting crude product may be purified by recrystallization from hexanes.

To a stirred solution of the brominated long-chain alcohols (1 equivalent) and potassium hydroxide (2.2 equivalents per bromine) in n-propanol (0.2 M) at 60° C., dimethyl sulfoxide (DMSO) (2.5 equivalents per bromine) may be added in one portion. The reaction mixture may be heated to reflux, stirred for about 4 hours, and poured over an ice and 2N HCl mixture. The resulting solid may be isolated via filtration, rinsed with water, and cold methanol. The product may be purified via column chromatography or other techniques.

Prophetic Example

Conversion of Internal Alkynes

To a stirred solution of the alkynyl long-chain alcohols in anhydrous 1,3-diaminopropane (1.0 M) under argon, a solution of potassium hydride dissolved in anhydrous 1,3-diaminopropane (1.5 M, 4.5 equivalents) may be added, dropwise. The reaction mixture may be stirred for about 4 hours, poured into cold 3N HCl, and extracted with diethyl ether (e.g., 3 times). The combined organic layers may be washed with 3N HCl (e.g., 3 times), dried over $MgSO_4$, and filtered through a pad of silica gel. The solvents may be removed in vacuo, and further purification may be performed using various techniques.

Prophetic Example

Conversion of Alkynes to Carbonyl Groups

To anhydrous tetrahydrofuran (THF) at about 0° C. under argon, a solution of borane (or 9-BBN, 1.0 M, 0.5-1 equivalents per carbonyl group) in THF may be added. While stirring, a solution of the terminal alkynyl long-chain alcohols in anhydrous THF (2.0 M) may be added, dropwise. The reaction mixture may be warmed to room temperature and stirred for about 2 hours. The reaction mixture may then be cooled to about 10° C., and a solution of NaOH (3.0 M, in excess) may be added, followed by hydrogen peroxide (30 weight percent in water, in excess). The reaction mixture may be heated to about 50° C. for about 2 hours and then cooled to room temperature. Diethyl ether may be added to the reaction mixture, and the layers may be separated. The aqueous layer may be extracted with diethyl ether (e.g., 3 times). The combined organic layers may be washed with 3N HCl (e.g., 3 times), dried over $MgSO_4$, and filtered through a pad of silica gel. The solvents may be removed in vacuo, and further purification may be performed according to various techniques.

Prophetic Example

Conversion of carbonyl groups to hydroxyl groups

To a stirred suspension of $NaBH_4$ (4 equivalents) in 500 mL of anhydrous THF at about 0° C., a solution of carbonyl-functionalized long-chain alcohols in 50 mL of anhydrous THF may be added, dropwise. The reaction mixture may be stirred for about 4 hours and quenched by dropwise addition of 2N HCl. The solids may be removed by filtration, and the layers of the filtrate may be separated. The aqueous layer may be rinsed with diethyl ether (e.g., 3 times), and the combined organic layers may be rinsed with $NaHCO_3$, brine, and dried over $MgSO_4$. The solvent may be removed in vacuo, and the resulting crude product may be purified by vacuum distillation or other purification techniques.

Thus, FIG. 1 illustrates an example of the preparation of a biorenewable polyurethane material from an unsaturated plant oil (e.g., an unsaturated vegetable oil). The process includes converting the unsaturated plant oil into unsaturated long-chain alcohols and converting internal alkenes of the unsaturated long-chain alcohols into terminal alkynes, which may be converted into terminal, primary hydroxyl groups (with no dangling chains). The elimination of the presence of the terminal aliphatic alkyl chains in the polyols of the present disclosure may enable formation of biorenewable polyurethane materials with improved mechanical properties.

Referring to FIG. 2, a particular embodiment of a process 200 of forming a biorenewable polyurethane material is illustrated. In FIG. 2, an unsaturated plant oil may be reduced to multiple unsaturated, long-chain alcohols, and internal alkenes of the unsaturated, long-chain alcohols may be "converted" into terminal alkynes (e.g., via an "alkyne zipper" reaction). The terminal alkynes may be converted into hydroxyl groups to form polyols having two primary hydroxyl groups and optionally one or more secondary hydroxyl groups (with no dangling chains). In the particular embodiment illustrated in FIG. 2, the polyol mixture may be polymerized to form a polyurethane material, and the polyurethane material may be chemically reacted with a diisocyanate cross-linking material to form a biorenewable polyurethane material.

The process 200 includes forming unsaturated long-chain alcohol(s) from an unsaturated plant oil via a reduction reaction, at 202. For example, referring to FIG. 1, the unsaturated plant oil may be reduced with a suitable reduction agent (e.g., LiAlH$_4$) to convert the triglyceride esters of the unsaturated plant oil to hydroxyl groups, resulting in three unsaturated, long-chain alcohols.

The process 200 includes forming alkyne-terminated long-chain alcohol(s) from the unsaturated, long-chain alcohols, at 204. For example, referring to FIG. 1, the internal alkene groups of the unsaturated, long-chain alcohols may be converted to internal alkyne groups in the second chemical reaction, and the internal alkyne groups may be converted to terminal alkynes in the third chemical reaction.

The process 200 includes forming polyol(s) having two primary hydroxyl groups (and optionally one or more secondary hydroxyl groups) from the alkyne-terminated long-chain alcohols, at 206. For example, referring to FIG. 1, the fourth chemical reaction illustrates that the terminal alkynes may be converted into carbonyl groups, and the fifth chemical reaction illustrates that the carbonyl groups may be reduced to hydroxyl groups.

The process 200 includes polymerizing a mixture that includes the polyols having the two primary hydroxyl groups to form a polyurethane material, at 208. For example, referring to FIG. 1, the mixture of polyols formed in the fifth chemical reaction may be polymerized to form a polyurethane material.

In the particular embodiment illustrated in FIG. 2, the process 200 includes chemically reacting the polyurethane material with a diisocyanate cross-linking material to form a biorenewable polyurethane material, at 210. For example, the polyurethane material that is formed via a polymerization of the mixture of polyols illustrated in FIG. 1 may be chemically reacted with a diisocyanate cross-linking material.

Thus, FIG. 2 illustrates an example of a process of forming a biorenewable polyurethane material. The process includes forming unsaturated, long-chain alcohols from an unsaturated plant oil via a reduction reaction. The process includes converting internal alkenes of the unsaturated, long-chain alcohols into terminal alkynes, which may be converted into terminal, primary hydroxyl groups (with no dangling chains). The elimination of the presence of the terminal aliphatic alkyl chains in the polyols of the present disclosure may enable formation of biorenewable polyurethane materials with improved mechanical properties. Further, secondary hydroxyl groups of the polyols may be available as cross-linking locations for chemical reaction with a diisocyanate cross-linking material.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein but is to be accorded the widest scope possible consistent with the principles and features as defined by the following claims.

The invention claimed is:

1. A process of forming a polyurethane material, the process comprising:
   forming unsaturated alcohols from an unsaturated plant oil via a reduction reaction;
   forming alkyne-terminated alcohols from the unsaturated alcohols via an alkyne zipper reaction;
   forming polyols having two primary hydroxyl groups from the alkyne-terminated alcohols by converting alkynes of the alkyne-terminated alcohols to hydroxyl groups; and
   performing a polymerization reaction using a mixture that includes the polyols to form a polyurethane material.

2. The process of claim 1, wherein the unsaturated plant oil includes an unsaturated vegetable oil.

3. The process of claim 1, wherein the unsaturated plant oil includes:
   a first fatty acid chain having at least one carbon-carbon double bond;
   a second fatty acid chain having at least one carbon-carbon double bond; and
   a third fatty acid chain.

4. The process of claim 3, wherein the first fatty acid chain has at least two carbon-carbon double bonds.

5. The process of claim 4, wherein the second fatty acid chain has at least two carbon-carbon double bonds.

6. The process of claim 3, wherein the third fatty acid chain has at least one carbon-carbon double bond.

7. The process of claim 6, wherein the third fatty acid chain has at least two carbon-carbon double bonds.

8. The process of claim 1, wherein the polyols include one or more secondary hydroxyl groups.

9. The process of claim 1, wherein performing the polymerization reaction using the mixture that includes the polyols comprises adding a diisocyanate material to the mixture.

10. The process of claim 9, wherein performing the polymerization reaction using the mixture that includes the polyols further comprises adjusting an amount of diisocyanate material in the mixture to adjust a degree of cross-linking in the polyurethane material.

11. The process of claim 9, wherein the diisocyanate material includes methylene diphenyl diisocyanate (MDI), toluene diisocyanate (TDI), hexamethylene diisocyanate (HDI), isophorone diisocyanate (IPDI), pentamethylene diisocyanate (PDI), or a combination thereof.

12. A biorenewable polyurethane material formed by a process comprising:
- forming unsaturated alcohols from an unsaturated plant oil via a reduction reaction;
- forming alkyne-terminated alcohols from the unsaturated alcohols via an alkyne zipper reaction;
- forming polyols having two primary hydroxyl groups from the alkyne-terminated alcohols by converting alkynes of the alkyne-terminated alcohols to hydroxyl groups; and
- performing a polymerization reaction using a mixture that includes the polyols to form a biorenewable polyurethane material.

13. The biorenewable polyurethane material of claim 12, wherein the unsaturated plant oil includes at least a first fatty acid chain having one or more carbon-carbon double bonds and a second fatty acid chain having one or more carbon-carbon double bonds, wherein the first fatty acid chain is associated with formation of a first polyol having two primary hydroxyl groups, and wherein the second fatty acid chain is associated with formation of a second polyol having two primary hydroxyl groups.

14. The biorenewable polyurethane material of claim 13, wherein the first fatty acid chain includes two or more carbon-carbon double bonds, and wherein the first polyol includes one or more secondary hydroxyl groups.

15. The biorenewable polyurethane material of claim 12, wherein a first fatty acid chain of the unsaturated plant oil has a first number of carbon-carbon double bonds, wherein a second fatty acid chain of the unsaturated plant oil has a second number of carbon-carbon double bonds, and wherein the first number of carbon-carbon double bonds is different from the second number of carbon-carbon double bonds.

16. The biorenewable polyurethane material of claim 12, wherein the polyols having the two primary hydroxyl groups include at least a first polyol having two primary hydroxyl groups and a second polyol having two primary hydroxyl groups and one or more secondary hydroxyl groups.

17. The biorenewable polyurethane material of claim 16, wherein the first polyol includes one or more secondary hydroxyl groups.

18. An acoustic dampening foam comprising:
- a petroleum-based first polyurethane material; and
- a second polyurethane material distinct from the first polyurethane material, the second polyurethane material formed by a process that includes:
  - forming unsaturated alcohols from an unsaturated plant oil via a reduction reaction;
  - forming alkyne-terminated alcohols from the unsaturated alcohols via an alkyne zipper reaction;
  - forming polyols having two primary hydroxyl groups from the alkyne-terminated alcohols; and
  - performing a polymerization reaction using a reaction mixture that includes the polyols to form a biorenewable polyurethane material, wherein the reaction mixture includes a diisocyanate material.

19. The acoustic dampening foam of claim 18, wherein a weight of the second polyurethane material is not less than 10 percent of a weight of the acoustic dampening foam.

\* \* \* \* \*